United States Patent [19]
Cheng et al.

[11] Patent Number: 5,627,080
[45] Date of Patent: May 6, 1997

[54] DETERGENT-FACILITATED IMMUNOASSAY FOR THE RAPID AND QUANTITATIVE ASSAY OF PHARMACOLOGICAL AGENTS

[75] Inventors: Anthony K. Cheng, Anaheim; Julie S. Kim, Placentia; Chan S. Oh, Chino Hills, all of Calif.

[73] Assignee: Beckman Instruments, Inc., Fullerton, Calif.

[21] Appl. No.: 283,116

[22] Filed: Jul. 29, 1994

[51] Int. Cl.$^6$ .................................................. G01N 33/546
[52] U.S. Cl. ........................ 436/534; 435/7.5; 435/962; 436/536; 436/805; 436/817; 436/826; 436/909
[58] Field of Search ................... 435/7.5, 962; 436/534, 436/536, 805, 807, 817, 826, 909

[56] References Cited

U.S. PATENT DOCUMENTS

| | | | |
|---|---|---|---|
| 4,140,662 | 2/1979 | Reckel et al. | 436/533 |
| 4,695,537 | 9/1987 | Dorsett | 435/5 |
| 5,162,236 | 11/1992 | Pang et al. | 436/517 |
| 5,168,057 | 12/1992 | Oh et al. | 435/174 |
| 5,196,351 | 3/1993 | Harris et al. | 436/501 |

FOREIGN PATENT DOCUMENTS

| | | |
|---|---|---|
| 0315317 | 10/1989 | European Pat. Off. |
| 0439611 | 8/1991 | European Pat. Off. |
| 0532757 | 3/1993 | European Pat. Off. |
| 0187862 | 11/1983 | Japan |
| 8807683 | 10/1988 | WIPO |
| 9010232 | 9/1990 | WIPO |

OTHER PUBLICATIONS

Bowden, R.A. et. al., "A Turbidimetric Latex Inhibition Immunoassay for Detergent Solubilized Lipopolysaccharide: Application to *Brucella* Cells," *J. Microbiol. Meth.* 16:297–306 (1992).

Goldring, O.L., "Detergent Solubilized Antigens in Enzyme Immunoassay with Particular Reference to Enzyme–Linked Immunosorbent Assay (ELISA) Systems," *Immunoassay Technol.* 2:189–214 (1986).

Bibb, W. et al., "Treatment of Human Serum with a Detergent/Solvent Combination for Inactivation of Human Immunodeficiency Virus (HIV) and Hepatitis B Virus (HBV) Prior to Determination of Antibody Levels to *Neisseria meningitis* Group of Polysaccharide by ELISA," *Abstr. Gen. Meet. Amer. Soc. Microbiol.* 91:396 (1991).

McCabe, J.P. et al., "The Effects of Detergent on the Enzyme–Linked Immunosorbent Assay (ELISA) of Blood Group Substances," *J. Immunol. Meth.* 108:129–135 (1988).

Noorduyn, L.A., "Favorable Effect of Detergent on Antigen Detection and Comparison of Enzyme Linked Detection Systems in an ELISA for *Chlamydia trachomatis*," *J. Immunoassay* 10:429–448 (1989).

*Primary Examiner*—Lora M. Green
*Assistant Examiner*—Susan C. Wolski
*Attorney, Agent, or Firm*—William H. May; Gary T. Hampson

[57] ABSTRACT

Methods for modulating the rates and dose responses of immunoassays through the incorporation of one or more detergents into the immunoassay reaction are disclosed. The methods are particularly suitable for automated immunoassay formats, especially with formats that use analyte-biotin bidentate reagents. The methods may be used to facilitate the detection of any desired, preselected pharmacological agent.

28 Claims, 1 Drawing Sheet fig.1

DETERGENT-FACILITATED IMMUNOASSAY FOR THE RAPID AND QUANTITATIVE ASSAY OF PHARMACOLOGICAL AGENTS

FIELD OF THE INVENTION

The invention concerns reagents and methods for facilitating the quantitative analysis of pharmacological agents in an immunoassay. Specifically, the invention concerns the use of detergents to achieve a desired assay sensitivity of immunoassays and assays with standardized reagents. The invention may be used to determine the concentration of desired, preselected pharmacological agents, such as cocaine, acetaminophen, digoxin, phenytoin, phenobarbital, etc.

BACKGROUND OF THE INVENTION

Immunoassays provide a means for determining whether an individual has been exposed to a pharmacological agent, a pathogen, or a substance of abuse (such as cocaine, opiates, etc.). Such determinations are of broad importance in medicine and law enforcement.

Immunoassays, are assay systems that exploit the ability of an antibody to specifically recognize and bind to a particular target molecule. Antibodies are immunoglobulins that are produced in response to the detection of a foreign substance ("antigen") within an animal. The region of an antigen that is recognized by an antibody, and which to which the antibody binds is referred to as an "epitope." Although large molecules, such as proteins or other molecules possess multiple epitopes, low molecular weight molecules, such as most pharmacological agents possess only a single epitope. Such low molecular weight molecules are referred to as "haptens." Immunoassays are used extensively in modern diagnostics (Fackrell, *J. Clin. Immunoassay* 8:213–219 (1985)). A large number of different immunoassay formats have been described (Yolken, R. H., *Rev. Infect. Dis.* 4:35 (1982); Collins, W. P., In: *Alternative Immunoassays*, John Wiley & Sons, New York (1985); Ngo, T. T. et al., In: *Enzyme Mediated Immunoassay*, Plenum Press, New York (1985)). Immunoassay formats have been developed that are amenable for large scale usage (for review, see Lee, T. T. T. et al., European Patent Application Publn. No. 203,238, herein incorporated by reference).

The simplest immunoassay involves merely incubating an antibody that is capable of binding to a predetermined molecule (i.e. an "analyte") with a sample that is suspected to contain the analyte. The presence of the target molecule is determined by the presence, and is proportional to the concentration, of any immune complexes that form through the binding of antibody and analyte. In order to facilitate the separation of such immune complexes from the unbound antibody initially present, a solid phase is typically employed. In more sophisticated immunoassays, the concentration of the target molecule is determined by binding the antibody to a support, and then incubating the bound antibody in the presence of the analyte-containing sample.

Target molecules that have become bound to the immobilized antibody can be detected in a variety of ways. For example, the support can be incubated in the presence of a labeled, second antibody (i.e. a "sandwich" immunoassay) that is capable of binding to a second epitope of the target molecule. Immobilization of the labeled antibody on the support thus requires the presence of the target, and is proportional to the concentration of the target in the sample. In an alternative assay, the sample is incubated with a known amount of labeled target and antibody binding site. Any target molecules present in the sample compete with the labeled target molecules for the antibody binding sites. Thus, the amount of labeled target molecules that are able to bind the antibody is inversely proportional to the concentration of target molecule in the sample. This is known as a competitive immunoassay.

The various immunoassay formats can be further divided into two main classes, depending upon whether the assay requires the separation of bound species from unbound species. Heterogeneous immunoassays require such purification, and hence entail a separation or isolation step. In contrast, homogeneous assays are designed such that the removal of bound from unbound species is unnecessary. Because homogeneous assays lack a separation step, and are more easily automated, they are more desirable than heterogeneous assays in applications that entail the screening of large numbers of patients.

One factor that attenuates the sensitivity of immunoassays is the degree of inaccessibility of the analyte being assayed. Analytes such as membrane associated proteins or liposaccharides are often significantly inaccessible to antibodies, and hence, their presence in a biological sample may escape detection. One partial solution to this problem has been to extract such insolubilized molecules using detergents. For example, Bowden, R. A. et al. discuss a turbidometric latex inhibition assay for detergent-solubilized lipopolysaccharides as a means for evaluating Brucella vaccine preparations (Bowden, R. A. et al., *J. Microbiol. Meth.* 16:297–306 (1992)). The use of detergents in enzyme linked immunosorbent assays is reviewed by Goldring, O. L. (*Immunoassay Technol.* 2:189–214 (1986)). Detergents have also been used in immunoassays of human immunodeficiency virus (HIV) and hepatitis B virus in order to inactivate the virus, and render the assay less hazardous to health care professionals (Bibb, W. et al., *Abstr. Gen. Meet. Amer Soc. Microbiol.* 91:396 (1991)). Detergents have also been used to facilitate the immobilization of antigens in agglutination immunoassays (Dorsett, P. H., U.S. Pat. No. 4,695,537).

Unfortunately, although the presence of detergent increases analyte accessibility, it decreases the rate and extent of immune complex formation (Goldring, O. L., *Immunoassay Technol.* 2:189–214 (1986); McCabe, J. P. et al., *J. Immunol. Meth.* 108:129–135 (1988); Noorduyn, L. A., *J. Immunoassay* 10:429–448 (1989)). Thus, the use of detergents has significant adverse consequences.

Regardless of immunoassay format, the utility of an immunoassay in detecting an analyte depends upon its capacity to report the extent of the formation of immune complexes between the antibody employed and the analyte whose presence or concentration is being measured. In general, two independent approaches exist for increasing this capacity. The first approach involves labeling one or more of the reagents. The second approach involves increasing the size of the immune complex.

A wide array of labels (such as radioisotopes, enzymes, fluorescent moieties, chemiluminescent moieties, or macroscopic labels, such as beads, etc.) have been employed in order to facilitate the detection of immune complexes (see, Chard., T., et al., In: *Laboratory Techniques and Biochemistry in Molecular Biology* (Work, T. S., Ed.), North Holland Publishing Company, New York (1978); Kemeny, D. M. et al. (Eds.), *ELISA and Other Solid Phase Immunoassays*, John Wiley & Sons, New York (1988)). Radioisotopes have long been used in immunoassays. O'Leary, T. D. et al., for example describe a radioimmunoassay ("RIA") for digoxin serum concentrations (O'Leary, T. D. et al., *Clin. Chem.* 25:332–334 (1979)). RIAs have the advantages of simplicity, sensitivity, and ease of use. Radioactive labels are of relatively small atomic dimension, and do not normally affect reaction kinetics. Such assays suffer, however, from the disadvantages that, due to radioisotopic decay, the reagents have a short shelf-life, require special handling and disposal, and entail the use of complex and expensive analytical equipment. The difficulty of handling such hazardous materials, and the problem of radioactive decay have led to the development of immunoassays that use other labels.

Enzymes, in particular, are now widely used as labels in immunoassay formats. Enzyme-linked immunoassays ("ELISAs") have the advantage that they can be conducted using inexpensive equipment, and with a myriad of different enzymes, such that a large number of detection strategies—colorimetric, pH, gas evolution, etc.—can be used to quantitate the assay. In addition, the enzyme reagents have relatively long shelf-lives, and lack the risk of radiation contamination that attends to RIA use. ELISAs are described in *ELISA and Other Solid Phase Immunoassays* (Kemeny, D. M. et al., Eds.), John Wiley & Sons, New York (1988), incorporated by reference herein. An enzyme-multiplied immunoassay technique (EMIT®, Syva Co.) has been used to analyze the presence of analytes in biological fluids. The procedure is based on a competition between an analyte and an analyte-enzyme conjugate, for binding sites on an antibody present in limiting amounts (Cone, E. J. et al., *J. Forens. Sci.* 35:786–781 (1990); Baugh, L. D. et al., *J. Forens. Sci.* 36:79–85 (1991); Standefer, J. C. et al., *Clin. Chem.* 37:733–738 (1991); Schwartz, J. G. et al., *Amer. J. Emerg. Med.* 9:166–170 (1991);Helper, B. et al., *Amer. J. Clin. Pathol.* 81:602–610 (1984); Cambell, R. S. et al., *J. Clin. Chem. Clin. Biochem.* 24:155–159 (1986); Khanna, P., U.S. Pat. No. 5,103,021).

In addition to enzymes, fluorescent moieties are frequently used as labels. A fluorescence polarization immunoassay format (TDx®, Abbott Laboratories, Inc.) has been found to be approximately equivalent to the EMIT®formats (Schwartz, J. G. et al., *Amer. J. Emerg, Med.* 9:166–170 (1991); Koizumi, F. et al., *Tohoku J. Exper. Med.* 155:159- (1988); Edinboro, L. E. et al., *Clin. Toxicol.* 29:241-(1991); Okurodudu, A. O. et al., *Clin. Chem.* 38:1040 (1992); Okurodudu, A. O. et al., *Clin. Chem.* 38:1040 (1992); Klotz, U., *Ther. Drug. Monitor.* 15:462–464 (1993)). Wong, S. H. Y., et al., have described the use of an automated (OPUS™) analyzer to measure digoxin concentration in a monoclonal antibody mediated, fluorescence-based assay protocol (Wong, S. H. Y. et al., *Clin. Chem.* 38:996 (1992)). Lee, D. H. et al. also disclose the use of a fluorescence polarization assay and a chemiluminescent assay format to assay digoxin levels (Lee, D. H. et al., *Clin. Chem.* 36:1121 (1990)).

As indicated, immunoassay sensitivity can be enhanced by increasing the size of the immune complex that is formed in the immunoassay. If the immune complex is large enough, it will become capable of scattering light, or of spontaneously precipitating. In such cases, agglutination, or nephelometric or turbidimetric immunoassay methods may be employed. Nephelometric methods measure the light scattered by a suspension of particles or reflected toward a detector that is not in the direct path of light (Sternberg, J. C., *Clin. Chem.* 23:1456–1464 (1977)). In contrast, turbidimetric methods measure the reduction of light transmitted through the suspension of particles or aggregates. The reduction is caused by reflection, scatter, and absorption of the light by the aggregates. In both nephelometry and turbidimetry, the rate of change in light scatter may also be measured, and provides an indication of the amount of antigen present. Agglutination assays measure the precipitation of antibody-antigen complexes. Such assays can be extremely sensitive, and are amenable to automation. Because nephelometric and turbidimetric methods do not require the separation of the initially present antibody from the immune complexes formed in the assay, such assays are homogenous immunoassays. An agglutination inhibition assay for cocaine is commercially available (OnTrak™, Hoffman-LaRoche) but appears to be substantially less efficient than the above methods (Schwartz, J. G. et al., *Amer. J. Emerg. Med.* 9:166–170 (1991)).

The requirement of producing large immune complexes has limited the applicability of nephelometric, turbidometric or agglutination immunoassays to high molecular weight molecules, such as proteins, that possess several epitopes. In particular, since many pharmacological agents have only a single epitope, they are incapable of forming the large immune complexes needed for such immunoassays.

One approach to this problem involves the agglutination of antibody-coated particles with a polyepitopic species (or a developer antigen) containing at least two covalently coupled hapten analogs (e.g., a protein carder, such as bovine serum albumin ("BSA") (Mongkolsirichaikul, D. et al., *J. Immunol. Meth:* 157:189–195 (1993)). The agglutination reaction requires the use of a polyepitopic species or a developer antigen because a molecule that has only one epitopic site cannot bind two antibodies, and hence cannot cross-link two antibodies together. Such cross-linking is an essential step in the formation of large immune complexes. A second approach involves the agglutination of hapten-coated particles.

In either method, the hapten or drug in the sample competitively binds to the antibody binding sites and results in inhibition or reduction of the immunoagglutination. Particle agglutination assays for therapeutic drugs and drugs of abuse which use hapten coated particles are commercially available. Examples of such assays are PETINIA™ (Du Pont) and AbuScreen™ (Roche), Advisor™ (Abbott) and that of Mitsubishi.

A solution to this problem has recently been described by Oh, C. S. et al. in U.S. Pat. No. 5,168,057, by Harris, P. C. et al. in U.S. Pat. No. 5,196,351, and by Oh, C. S. et al., In: Nonisotopic Immunoassay, Ngo, T. T. (Ed.), Plenum Press, New York, pp. 457–476 (1988), all herein incorporated by reference, and involves the use of bidentate or tridentate analyte reagents. In bidentate immunoassay methods, the immune complex forms through two distinct binding reactions. One reaction involves the binding of the biotin member of the bidentate to an anti-biotin antibody (or a fragment of such an antibody), or to streptavidin or avidin. The other reaction is the immunoreaction of an anti-analyte antibody to the analyte member of the bidentate. Because antibody has two hapten binding sites, and avidin has four biotin binding sites, an immunocomplex is formed when the antibody, bidentate reagent, and avidin are mixed together. The formation of the immunocomplex is rapid and appears to be associated with the positive charge (pI 10) of the approximately thirty five lysine termini of avidin in addition to the strong binding of avidin and biotin. This specific charge-assisted immunoprecipitin reaction is a characteristic feature of the biotin-avidin methodology. Under similar conditions, streptavidin (pI 5) or charge neutralized avidin fails to produce the immunoprecipitin reaction with high rate.

In practice, steric hindrance between the F(ab) portion of the antibody (i.e., the hapten binding portion of the antibody) and avidin may block some of the avidin's four biotin-binding sites. Such blockage restricts both the rate and extent of immune complex formation. For example, if the spacer length between the hapten and biotin is less than about 27 Å, steric hindrance between avidin and the Fab portion of the antibody will block two of avidin's four biotin binding sites (Oh, C. S. et al., In: Nonisotopic Immunoassay, Ngo, T. T. (Ed.), Plenum Press, New York, pp. 457–476 (1988)). Such blockage causes the immune complex to be linear. The linear polymer results in a turbidity change or in light scattering which can be monitored on a turbidimeter or nephelometer, respectively. If hapten is present in the sample, it will compete for antibody with the hapten member of the bidentate reagent. Such competition leads to a reduction in the rate of immune complex formation. Thus, the rate of the nephelometric or turbidimetric response becomes inversely proportional to the concentration of the hapten in the sample.

Despite the success of the methods of Oh, C. S. et al. (U.S. Pat. No. 5,168,057) and Harris, P. C. et al. (U.S. Pat. No. 5,196,351) methods that would further improve both the rate of immune complex formation, and the resultant dose response of the immunoassay would provide more efficient and effective immunoassays for determining the concentration of medically important pharmacological agents. The present invention provides reagents and methods for conducting such improved immunoassays.

SUMMARY OF THE INVENTION

The invention relates to detergents and other reagents that can be incorporated into immunoassays in order to improve the rate of immune complex formation and thereby throughput, and to improve the dose response to desired assay sensitivity. The invention encompasses assay compositions and methods for conducting such improved immunoassays.

In detail, the invention provides an assay for determining the presence of a target analyte in a test sample comprising the steps of:

(A) forming a reaction mixture by contacting a test sample with an anti-target analyte antibody; and a detergent, wherein the detergent is present in the reaction mixture at a concentration greater than about 1%;

(B) incubating the reaction mixture under conditions sufficient to permit the formation of a complex between any of the analyte in the reaction mixture and the anti-target analyte antibody; and (C) determining the presence of the target analyte in the test sample by measuring the extent of any formation of the complex, the extent being proportional to the concentration of the target analyte in the sample.

The invention also includes the embodiment of the above assay, wherein in the step (A), the formed reaction mixture additionally contains:

(i) a soluble bidentate reagent comprising a biotin member, an analyte member, and a spacer member between the biotin and analyte members, wherein:

(a) the biotin member of the reagent is capable of binding to a biotin-binding agent selected from the group consisting of avidin and streptavidin; the biotin-binding agent being immobilized to a solid support.

(b) the analyte member of the reagent is capable of specifically binding to an antibody capable of binding to the target analyte;

(c) the intermediate spacer member is sufficient in length to permit the analyte member to bind to an anti-target analyte antibody and the biotin member to bind to a biotin-binding ligand; and (ii) the biotin binding agent, and wherein in the step (C), the presence of the target analyte in the test sample is determined by measuring the extent of any formation of the complex, the extent being inversely proportional to the concentration of the target analyte in the sample.

The invention is also directed to the embodiments of such assays wherein the detergent is present at a concentration greater than about 2%.

The invention is also directed to the embodiments of such assays wherein the detergent is a non-ionic detergent, such as an alkylpolyoxyethylene, an alkylphenylpolyoxyethylene ether (especially Triton-™), an acylpolyoxyethylene sorbitan ester (especially Tween-20™).

The invention is particularly directed to the embodiments of such assays wherein the immobilized support is a latex support, such as a carboxylate modified latex particle having a diameter of about 60 nm.

The invention particularly concerns the embodiments of the above-described assays wherein the assay is conducted using assay processing apparatus that lack automated or semi-automated sample dilution capability.

The invention is also directed to the embodiments of such assays wherein the analyte is a pharmacological agent such as phenytoin or Phenobarbital, and the assay is capable of detecting such analyte in the sample.

DESCRIPTION OF THE PREFERRED EMBODIMENTS

The present invention concerns improved assays and reagents that can be used in immunoassay formats to measure the concentration of a preselected agent in a sample with optimized sensitivity and greater speed, and which provide a more efficient immunoassay. The invention is particularly amenable to immunoassays that detect and quantify low molecular weight analytes, such as pharmacological agents. The methods of the present invention are thus particularly relevant for assays of small haptenic analytes such as benzoylecgonine, cocaine, digoxigenin, primidone, acetaminophen, vancomycin, opiates, cannabinoids, theophylline, phenobarbitol, a minoglycoside antibiotics, phenytoin, quinidine, carbamazepine, etc.

The immunoassays of the present invention may be used to assay the presence or concentration of analytes in biological samples (such as blood, serum, sputum, urine, cerebrospinal fluid (CSF), etc.) as well as forensic samples (such as clothing, chemical residues, dust or powders, etc.).

In its most preferred embodiment, the immunoassays of the present invention will employ monoclonal antibodies. Most preferably, such antibodies are generated by immunizing a mouse with the analyte of interest conjugated to an antigenic protein, or in concert with an adjuvant, harvesting the splenic leukocytes of the animal, and fusing them with a suitable myeloma cell. In one embodiment, such monoclonal antibodies can be directly employed in an immunoassay format. Alternatively, such antibodies may be cleaved or processed to form fragments that retain the capacity to bind the analyte. Examples of such fragments include (F(ab'), F(ab')₂ fragments.

The improvement in assay dose response and the concomittant increase in reaction rate of the present invention unexpectedly results from the incorporation of a detergent, or a mixture of detergents, into the immunoassay reaction. As indicated above, detergents have previously been employed in immunoassays, for example, to solubilize membrane-bound and otherwise insoluble antigens, but such use had been found to attenuate assay efficiency (Goldring, O. L., *Immunoassay Technol.* 2:189–214 (1986)). McCabe, J. P. et al. (*J. Immunol. Meth.* 108.:129–135 (1988)) reported that the presence of excess Triton X™ or octyl b-glucoside detergent in an immunoassay interfered with ELISAs by blocking binding sites on the microtiter plates. In that study, increasing detergent concentration from about 3 mM to about 300 mM decreased assay sensitivity by 85 fold. In particular, detergent concentrations in excess of the concentration needed to promote micelle formation (the "CMC" concentration) were found to be disadvantageous. For nonionic detergents such as Triton X™, the CMC is approximately 23 mM in water or buffer (2M Tris, pH 10.2) (McCabe, J. P. et al., *J. Immunol. Meth.* 108:129–135 (1988)) Noorduyn, L. A. (*J. Immunoassay* 10:429–448 (1989)) reported that octyl b-glucoside could provide a 2–4 fold increase in immunoassay sensitivity, but only if employed within a narrow range of concentration centered as about 0.5% (w/v). A similar improvement was observed using sodium desoxycholate at a concentration centered about 0.07% (w/v).

In contrast to such studies, the incorporation of detergent (s) has been found to improve the assay dose response without adversely affecting the reaction rate, and to thereby facilitate the development of automated immunoassays which can employ standardized reagents. The detergent(s) that may be employed in accordance with the methods of the present invention include anionic detergents, cationic detergent(s), zwitterionic detergents and nonionic detergents. The detergents may be added to the assay buffer or in the antibody diluent or in the diluent of other immunoassay reagents.

Suitable anionic detergents include sodium dodecyl sulfate (SDS) (Plumley, F. G. et al., *Anal. Biochem.* 134:86–95 (1983)); Krammer, K., *Immunol.* 48:799–808 (1983))., sodium dodecyl sulfonate (Helenius, A. et al., *Biochim, Biophys. Acta* 415:28–79 (1975)), sodium desoxycholate (Helenius, A. et al., *Enzymol.* 56:734–749 (1979)); etc.). Suitable cationic detergents include cetyltrimethylammonium bromide (CTAB) (Krammer, K., *Immunol.* 48:799–808 (1983)), and the like. Examples of suitable zwitterionic detergents include: Zwittergent™ (Calbiochem-Behring Diagnostics, Inc.), CHAPS (Perdew, G. H. et al., *Anal. Biochem.* 135:453–455 (1985)), lysophospholipids (Helenius, A. et al., *Enzymol.* 56:734–749 (1979)) and the like.

Nonionic detergents are the preferred detergents of the present invention. Examples of suitable nonionic detergents include alkylpolyoxyethylene ethers (such as BRIJ™ (Atlas Chemical Industries, Inc.); emulphogene™ (GAF Corp.), PX™ (Lubrol 12 A9:ICI), WX™ (Lubrol 17 A17:ICI), etc.), alkylphenylpolyoxyethylene ethers (such as Triton X™ (Rohm and Haas Company), octyl b-glucosides, Nonidet 40™ (Schlesinger Chemical Mfg. Company), Tergitol™ (Union Carbide Corp.); Igepal™ (GAF Corp.), etc.), and acylpolyoxyethylene sorbitan esters (such as Tween 20™ (Atlas Chemical Industries, Inc.) The alkylphenylpolyoxyethylene ethers are particularly preferred. Triton X™ (Rohm and Haas Company) is the most preferred detergent of the present invention.

The inclusion of such detergent permits one to modulate the sensitivity of immunoassays so as to obtain an assay that exhibits a more desirable reaction rate and dose response. A set of particularly "desired assay parameters" for immunoassays are that they exhibit:

(1) a rate of greater than about 0.2 Δ(O.D. units)/min at an analyte concentration of 0 μg/ml (the term "O.D." denotes optical density or absorbance).

(2) a reaction rate of greater than about 0.02 Δ(O.D. units)/min at the highest calibrator concentration.

(3) a dose response (as represented by "% B/B$_o$") of about 75–85% at the lowest non-zero calibrator concentration, and of less than 25% at the highest calibrator concentration. The term "%B/B$_o$" denotes the percentage of the ratio of the rate at a particular concentration to the initial rate.

(4) a capacity to measure analyte concentrations across an entire physiologically or otherwise relevant assay measuring range.

The inclusion of detergent(s) in the immunoassay reaction permits one to define immunoassays that exhibit these desired parameters.

Although the improvement resulting from the use of detergents is a general one, applicable to all immunoassay formats, the use of detergent(s) is particularly suited to the nephelometric and turbidometric assays such as those of Oh, C. S. et al. (U.S. Pat. No. 5,168,057), Harris, P. C. et al. (U.S. Pat. No. 5,196,351. In such nephelometric and turbidometric immunoassays, it is desirable to employ reaction conditions that yield comparable rates and dose responses regardless of the analyte being analyzed. Such is particularly desirable if automated processors are employed.

As described by Cheng Yan, Chan S. Oh and Anthony Cheng in U.S. patent application Ser. No. 248,479 filed on May 23, 1994, and entitled "REAGENTS AND METHODS FOR THE RAPID AND QUANTITATIVE ASSAY OF PHARMACOLOGICAL AGENTS," herein incorporated by reference in its entirety, the efficiency of the immunoassays of Oh, C. S. et al. (U.S. Pat. No. 5,168,057) and Harris, P. C. et al. (U.S. Pat. No. 5,196,351) can be further improved through the use of particles that have been labeled with a biotin-binding agent such as avidin. The methods of the present invention can be used to improve such an immunoassay. In particular, they may be used to improve the assay parameters of the novel two-site or "sandwich" immunoassays for haptenic analytes described by Yan, C et al In a sandwich assay, one component of the reaction (either the antigen, or an antibody that binds to the antigen) becomes bound (i.e. "sandwiched") by a second antibody. In the sandwich assays of Yan, C. et al., the bidentate reagent (by virtue of the binding of its analyte member and its biotin member) becomes "sandwiched" by an anti-analyte antibody and a biotin binding molecule. Significantly, such a structure differs from that created in conventional "sandwich" assays in that it may form using only a single antibody species.

The particles employed in accordance with the methods of Yan, C. et al. are macroscopic particles, preferably made of latex. The use of such macroscopic particles decreases the extent of complex formation needed to obtain a discernible change in light scatter or reflection. Thus, because of the presence of the macroscopic particles, immune complexes that would otherwise be too small to be detectable can be readily measured. The presence of the particles affects both the rate of detectable complex formation, and the lower limit of analyte that can be detected using nephelometric or turbidimetric methods.

The size of the latex particle can vary from less than 50 nm to more than 100 μm. The use of small particles (38–100 nm) is preferred for immunoassays that measure analyte concentration by turbidometric or nephelometric means. In such immunoassays, the use of 60–100 nm particles is particularly preferred. Such particles are obtainable from Seradyn, Inc., Indianapolis, Ind., US. Each 60 nm particle contains on the average approximately 10,000 carboxyl groups and each 100 nm particle carries approximately 25,000 groups available for covalent coupling.

Optimal coupling of avidin to carboxylated latex particles can be attained by monitoring the avidin to latex ratio, the pH of the reaction medium, and inclusion of detergent. The preferred coupling procedure involves two steps: the activation of carboxyl groups with carbodiimide and N-hydroxysuccinimide followed by reaction with avidin. Since avidin has an isoelectric point (pI) of 10, the pH of the second step of the reaction is preferably maintained slightly basic (pH 8.5 to 9). Such conditions ensure that a sufficient number of avidin molecules will remain in their free base form, and will thus be available for nucleophilic reaction with the activated carboxylated groups on the latex particles. At pH 8 or lower, latex particles may begin to agglutinate as soon as avidin is added. Some agglutination occurs at low pH, perhaps due to the charge interactions between avidin and the latex particle or capture of the particles by avidin via physical adsorption. Overloading the particles with avidin at pH 8.5 to 9 can also result in particle agglutination. When Tween-20 is used as the detergent at 0.13% in the reaction mixture, a total of 150 molecules of avidin per latex particle has been found to be optimal for coupling to the 60 nm particles obtained from Seradyn, Inc. Unless more Tween-20 is used, avidin in excess of this amount can undesirably induce agglutination of the particles. The 100 nm particle has a larger surface area and, in spite of its lower carboxyl content per unit weight of latex, carries about twice the number of carboxyl groups as the 60 nm particles. With the 100 nm particles, as much as 700 avidin molecules per particle can be used for the coupling reaction.

The avidin-labeled particles can be produced by incubating latex particles in the presence of N-hydroxysuccinimide and carbodiimide at 4° C. The pH of the mixture is then raised to about 9.0, and avidin is added. The latex-avidin complex can be recovered by chromatographic means (such as by Sepharose CL-6B purification, or ultrafiltration using large pore membranes), preferably after dialysis to remove the coupling reagents.

In a particularly preferred method for coupling these reagents, carboxylated latex is suspended in a solution of approximately 0.1M [3(N-morpholino)] propanesulfonic acid ("MOPS") (pH 6.0), approximately 0.5% polyoxyethylene (20) sorbitan ("Tween-20") (pH 6). The suspension is cooled to approximately 4° C. and provided with 1/9 volume of cold 0.1M MOPS (pH 6) containing 63 mg/ml of N-hydroxysuccinimide. One tenth volume of 0.1M MOPS (pH 6) containing 46 mg/ml of a water soluble carbodiimide is then added. The resulting mixture is then adjusted to pH 5.5–6, and stirred for approximately 1 hour at about 4° C. Thereafter, the pH is raised to about 9, and the reactants are permitted to react for an additional 5 hours with about 2 volumes of cold 0.02M borate buffer (pH 9) containing dissolved avidin at about 0.6 mg/ml.

BSA is then added to a final concentration of approximately 2 mg/ml, and the solution is stirred overnight at about 4° C. After this incubation, the latex-avidin mixture is dialyzed against 3 changes of 0.02M Tris (pH 9) buffer, containing 0.2% Tween-20 for 1.5 days, and purified, either by passage through a sepharose CL-6B column, or by other means (such as the Pellicon Cassette system (PCS)) and membrane having a molecular weight cutoff (MWCO) of 300 k. Such avidin-labeled particles may be used in conjunction with any of the immunoassay formats described herein that employ a biotinylated bidentate reagent.

Heat stressing the latex-avidin before coupling to the bidentate or the latex-avidin-bidentate conjugate itself for 3 to 6 days at 45° C. enhances the immunoreactivity and assay sensitivity in terms of steeper dose response.

As described by Yan, C. et al in U.S. patent application Ser. No. 248,479, two embodiments of the particle-enhanced immunoassay are particularly preferred: a 3-reagent system, and a 2-reagent system. The embodiments are described with reference to avidin, however, as indicated above, other biotin-binding agents may be employed.

In the "3-reagent system" embodiment, the immunoassay is conducted using three components: the avidin-labeled particles, the bidentate and the anti-analyte antibody. The formation of an immune complex is dependent upon the binding of the latex-avidin particles to the biotin portion of the bidentate, and the binding of the anti-analyte antibody to its binding site on the analyte portion of the bidentate. Extensive complex formation is possible because both the antibody and the latex avidin particles are capable of binding multiple bidentate molecules. Because the analyte has only a single epitope, the presence of analyte in the sample being evaluated blocks immune complex formation by competing with the bidentate for antibody binding sites. The extent of complex formation is thus inversely proportional to the concentration of analyte in the sample.

In the "2-reagent system" embodiment, the immunoassay is conducted using only two components: an avidin-labeled particle in which all biotin binding sites have been saturated with the biotin member of a bidentate biotin-analyte reagent, and an anti-analyte antibody. In this embodiment, the latex-avidin particles are preincubated with the bidentate under conditions of bidentate excess, such that substantially all of the biotin binding sites are filled with the biotin member of the bidentate. After removal of the excess bidentate by size exclusion column chromatography, dialysis, or other means, the resulting latex-avidin-analyte particle will thus be conjugated to the bidentate in a manner that permits the analyte portion of the bound bidentate to be accessible for subsequent binding with an anti-analyte antibody. This reagent can thus serve as the conventional "developer antigen" in an inhibition immunoassay and hence can form an immune complex when incubated in the presence of anti-analyte antibody. As in the 3-reagent system, the presence of analyte in the sample being evaluated will compete for analyte binding sites, and will attenuate the extent of complex formation. The extent of immune complex formation is inversely proportional to the concentration of analyte in the sample.

The particle-enhanced bidentate assay offers several advantages as compared to the liquid formulated bidentate method. The use of particles provides better sensitivity and requires less reagent and smaller sample volumes than in the liquid-based methods. An improvement of a factor of 10 or more in antibody usage and a reduction of 1.3 to 5 times in sample volume can be achieved for the same or a steeper dose response. The use of more diluted antibody and less sample also lowers contribution background signal from these materials and sample-to-sample matrix variations. Such use additionally reduces interference from the sample and antibody matrices including non-specific precipitations and provides greater flexibility with regard to the selection of a suitable calibrator matrix. For example, lipemic samples or triglyceride-rich samples interfere substantially with the liquid formulated bidentate assays. At triglyceride concentrations of 250 mg/dl or higher, a quantitation error of more than 10% in the measurement of analyte concentration has been observed. Such interference was not observed with the latex formulation.

One salient characteristic of the methods of the present invention is that they permit the use of a common sized particle in assays of different analytes. Previously, in order to obtain immunoassays that satisfied desired rate and dose response criteria, it was often necessary to employ different sized particles in order to assay each of a set of different pharmacological agents. The use of multiple sized particles increase the complexity of analysis, as well as the cost of production and verification of the particles. In contrast, the capacity to employ particles of the same size, and charge density, regardless of the analyte being evaluated, permits greater uniformity and lowers the attendant costs of the assays. This feature is particularly important with regard to sample processing systems, such as the Synchron (Beckman Instruments) that lack automated or semi-automated sample dilution capability, since it permits one to conduct multiple immunoassays without the need for adjusting or diluting sample or analyte concentrations.

Regardless of format, the processing of the immunoassay is most preferably automated using an automated sample processing system. Although any suitable system may be employed using the bidentate reagents of the present invention, the automated method of Pang, W. S. et al. described in U.S. Pat. No. 5,162,236 (herein incorporated by reference) is particularly preferred. In general, the method of Pang et al. employs an apparatus to control the temperature and volume of the reagents. The immunoassay is conducted in a cuvette within a nephelometric optics module. A sensor of the apparatus senses the temperatures of reaction buffer liquids as they flow into the cuvette, and a heat exchanging device increases or decreases the temperatures of the buffer liquids, as necessary. A control circuit responsive to the temperature sensor controls the heat exchanging device to maintain the temperature of the buffer liquids and the cuvette within a selected temperature range. The system preferably includes a sample pickup station, a sample probe for withdrawing a selected sample from the sample pickup station, a sample preparation station, and a sample transport for carrying said sample from the sample preparation station to the reaction cuvette. In preferred embodiments, the system also includes an antibody pickup station, an antibody probe for withdrawing an antibody from the antibody pickup station, an antibody preparation station, and an antibody transport for carrying the antibody from the antibody preparation station to the reaction cuvette.

Having now generally described the invention, the same will be more readily understood through reference to the following examples which are provided by way of illustration, and are not intended to be limiting of the present invention, unless specified.

EXAMPLE 1

Synthesis Of A Phenytoin-Biotin Bidentate

Phenytoin is an anticonvulsant agent used in the treatment of epilepsy and other affective diseases (Philip, J. et al., In: Analytical Profiles of Drug Substances," vol. 13, Florey, K. et al. (eds.), Academic Press, New York (pp. 417–445 (1984); Dreifus et al., Amer. Heart J. 80:709–713 (1970), both herein incorporated by reference). Because phenytoin is a potential carcinogen (IARC Monogr. 13:201–225 (1977)), it is important to monitor patient phenytoin levels so as to avoid overdosage.

The methods of Yan, C. et al. (U.S. patent application Ser. No. 248,479 were used to produce a phenytoin-biotin bidentate. This novel bidentate was used to define a detergent-facilitated, latex-enhanced homogeneous immunoassay, and to compare such assay with a non-detergent facilitated homogeneous immunoassay, for their relative abilities to screen for the presence of phenytoin in blood or serum samples.

Figure 1:
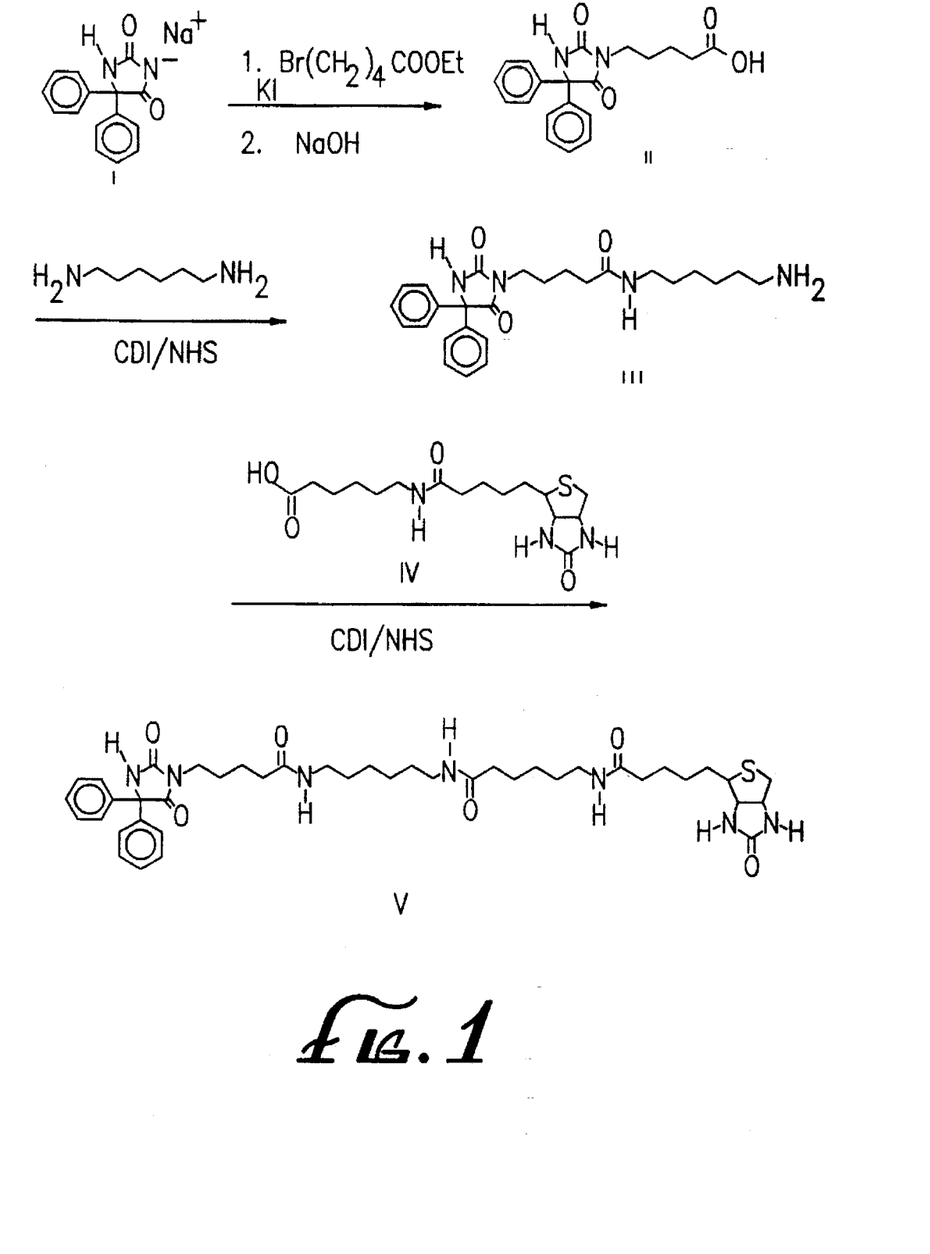
FIG. 1 shows the synthesis of a phenytoin-biotin bidentate.

The synthesis of the novel phenytoin-biotin bidentate is shown in FIG. 1. With reference to FIG. 1, phenytoin (I) was N-alkylated with w bromovalerate followed by hydrolysis in NaOH to yield the phenytoin acid derivative (II). The phenytoin acid derivative (II) was then coupled with hexanediamine using carbonyldiimidazole (CDI) and N-hydroxysuccinimide (NHS) to give a phenytoin amine derivative (III). The phenytoin amine derivative (III) was then coupled to a carboxylic acid biotin derivative (IV) using CDI and NHS to yield the desired phenytoin-biotin bidentate (V).

EXAMPLE 2

Use Of 100 Nm Latex Particles In A Latex Particle-Enhanced

Homogeneous Immunoassay For Phenytoin

The phenytoin-biotin bidentate was used to detect phenytoin in serum samples using both the above-described 3-reagent system configuration and the 2-reagent system configuration. In both assays, analysis was conducted using a Synchron analyzer.

Detection of phenytoin was accomplished using anti-phenytoin monoclonal antibodies produced from hybridoma clones AS3 or AS8. The antibodies produced from these clones are substantially equivalent. Suitable alternative monoclonal antibodies can be obtained commercially from BioSpecific, Inc. and BioDesign, Inc., or from other sources, such as those listed in the Linscott's Directory.

In the 3-reagent system configuration, the bidentate (V) itself was used to trigger the immunoreaction (i.e., as the trigger reagent). The assay thus consisted of three reagent components:

a. phenytoin-biotin bidentate-avidin conjugate (diluted in Tris buffer (0.02M, 0.2% Tween-20, 0.2% BSA, pH 9.0))

b. monoclonal anti-phenytoin antibody (produced by clone AS8) and diluted 1:50 with the ARRAY Antibody Diluent)

c. latex-avidin particles (diluted in Tris buffer (0.02M, 0.2% BSA, pH 9.0). The latex material (100 nm) was purchased from Seradyn. The latex particle was coupled to avidin to give the latex-avidin material using a mass ratio of 0.3 mg of avidin to 1 mg of latex.

The assay buffer was a mixture of 80% Apo Diluent (Beckman Instruments) and 20% Rheumatoid Buffer (Beckman Instruments). Calibrators were prepared in delipidized human serum. The Synchron analyzer was configured in the following manner for the 3-reagent assay:

a. Assay Buffer in Reagent Cartridge Compartment A: 220 µl b. Antibody (1/50)/Latex Avidin Mixture (1:1 by vol) in Compartment B: 62 µl c. Sample: 3 µl (neat)

d. Phenytoin-Biotin Bidentate (1.5 µg/ml) as trigger in Compartment C: 20 µl e. Trigger Add Time: 16 sec after addition of sample f. Reaction Read Window: 8 seconds after addition of trigger for 36 seconds g. Detection wavelength: 340 nm The assay was conducted using several standards in order to define a standard curve. The values of the standard curve are shown in Table 1 (O.D. =optical density (absorbance); Min=minute; % B/B$_0$ is the percentage of the ratio of an indicated rate relative to the initial reaction rate).

TABLE 1

| Standard (µg/ml) | ΔO.D./Min. | % B/B$_0$ |
|---|---|---|
| 0 | 0.26097 | 100 |
| 2.5 | 0.19798 | 75.9 |
| 5.0 | 0.13645 | 52.3 |
| 10 | 0.06723 | 25.8 |
| 20 | 0.02986 | 11.4 |
| 40 | 0.01622 | 6.2 |

The above-described 3-reagent assay was conducted in parallel with a TDx assay on a group of 38 patients. A good correlation was found between the 3-reagent Synchron values and those obtained using the TDx format. The analysis gave the following correlation equation:

Synchron=1.00(TDx)+0.1 r=0.9470 n=38

As indicated, the Synchron immunoassay was also performed using the above-described 2-reagent configuration. The 2-reagent assay configuration consisted of the latex-avidin-biotin-phenytoin conjugate and the antibody to produce the latex-agglutination reaction. Thus, in the 2-reagent assay format, the phenytoin-biotin bidentate was formulated as a conjugate component. The assay used the following reagents and buffers:

a. Monoclonal phenytoin antibody AS8 produced by Beckman Instruments was used. The antibody was diluted 1:50 with the ARRAY Antibody Diluent (Beckman P/N 668579) for assays.

b. Latex-Avidin-Biotin-Phenytoin conjugate (diluted in Tris buffer (0.02M, 0.2% Tween-20, 0.2% BSA, pH 9.0). The latex material (100 nm) was purchased from Seradyn. The latex particle was coupled to avidin using a mass ratio of 0.3 mg of avidin to 1 mg of latex. The latex-avidin was then complexed with the phenytoin bidentate to give the desired conjugate.

The assay buffer was a mixture of 70% Apo Diluent (Beckman Instruments) and 30% Rhematoid Buffer (Beckman Instruments). Calibrators were prepared in delipidized human serum. The Synchron analyzer was configured in the following manner for the 2-reagent assay:

a. Assay Buffer in Reagent Cartridge Compartment A: 220 µl b. Latex-Avidin-Phenytoin-Biotin Conjugate in Compartment C: 45 µl c. Sample: 3 µl (neat)

d. Antibody trigger in Compartment B: 30 µl e. Trigger Add Time: 16 sec after addition of sample f. Reaction Read Window: 8 seconds after addition of trigger for 36 seconds g. Detection wavelength: 340 nm The assay was thus conducted using several standards in order to define a standard curve. The values of the standard curve are shown in Table 2.

TABLE 2

| Standard (µg/ml) | ΔO.D./Min. | % B/B$_0$ |
|---|---|---|
| 0 | 0.30155 | 100 |
| 2.5 | 0.25640 | 85.0 |
| 5.0 | 0.18894 | 62.7 |
| 10 | 0.14687 | 48.7 |
| 20 | 0.09664 | 32.0 |
| 40 | 0.05111 | 16.9 |

The above-described 2-reagent assay was conducted in parallel with a TDx assay on a group of 62 patients. A good correlation was found between the 2-reagent Synchron values and those obtained using the TDx format. The analysis gave the following correlation equation:

Synchron=1.10(TDx)-0.1 r=0.9798 n=62

A comparison was conducted in order to determine the effect of latex-avidin particles on assay sensitivity or assay requirements. Thus, the 2-reagent Synchron assay for phenytoin was conducted with and without the above-described latex-avidin particles. Both assays used the same anti-phenytoin monoclonal antibody (produced by hybridoma clone AS3). The assays were conducted under the optimized conditions shown in Table 3.

TABLE 3

| | Formulation | |
|---|---|---|
| Reagent/Parameter | Liquid | Latex-Enhanced |
| Assay Buffer | 60% ICS Buffer 40% ICS Diluent | 0.02M Tris, pH 9.0 0.2% Tween-20 0.2% BSA |
| Assay Buffer Volume | 235 µl | 230 µl |
| Avidin-biotin-phenytoin conjugate (in Assay Buffer) | 32 µl | |
| Latex-Avidin-biotin-phenytoin conjugate (in Assay Buffer) | | 42 µl |
| clone AS3 Antibody Dilution | 1/3.25- | 1/100 |
| Antibody Volume | 45 µl | 30 µl |
| Sample volume | 3 µl | 3 µl |
| Trigger | Antibody | Antibody |
| Trigger Add Time | 16 seconds after addition of sample | |
| Reaction Read Window | 8 seconds after addition of trigger for 32 seconds | |
| Detection wavelength | 340 nm | 340 nm |

The assay conducted without latex particles (i.e., the "liquid-formulated phenytoin bidentate assay") was found to have required an antibody dilution of 1/3.25. In contrast, when the avidin was coupled to latex particles (i.e., in the "latex-enhanced" immunoassay formulation), an antibody dilution of 1/100 could be employed. Thus, the liquid formulated assay required at least thirty times more antibody than was required in the "latex-enhanced" immunoassay formulation. Moreover, the liquid formulation resulted in a much less sensitive dose-response as compared to the latex formulation.

The assays were evaluated using a set of phenytoin standard solutions in order to define standard curves for the liquid-formulated and the latex-enhanced assay. The standard curves are presented in Table 4.

TABLE 4

| Standard | Liquid-Formulation | | Latex-Enhanced | |
| --- | --- | --- | --- | --- |
| (µg/ml) | ΔO.D./Min | % B/B$_0$ | ΔO.D./Min | % B/B$_0$ |
| 0 | 0.31183 | 100 | 0.45152 | 100 |
| 2.5 | 0.28274 | 90.1 | 0.18168 | 45.2 |
| 5.0 | 0.25311 | 81.1 | 0.09175 | 22.8 |
| 10 | 0.20903 | 67.0 | 0.04749 | 11.9 |
| 20 | 0.12627 | 40.5 | 0.01911 | 4.7 |
| 40 | 0.039901 | 12.8 | 0.01091 | 2.7 |

The results of the liquid formulation and latex-enhanced assays indicated that either assay could be used to accurately determine phenytoin concentrations.

EXAMPLE 3

Optimization Of Assay Parameters For A Latex Particle-Enhanced Homogeneous Immunoassay For Phenytoin Using 100 Nm Latex Particles As indicated above, a highly preferred immunoassay for phenytoin will exhibit the certain "desired assay parameters: " a rate of greater than about 0.2 Δ(O.D. units)/min at an analyte concentration of 0 µg/ml; a reaction rate of greater than about 0.02 Δ(O.D. units)/min at the highest calibrator concentration; and a dose response (as represented by % B/B$_0$) of about 75–85% at the lowest non-zero calibrator concentration, and of less than 25% at the highest calibrator concentration. For phenytoin, the lowest physiologically relevant non-zero calibrator concentration is about 2.5 µg/ml; the highest physiologically relevant non-zero calibrator concentration is about 40 µg/ml.

In order to define such a preferred immunoassay, the effect of the avidin-to-particle loading ratio ("A/C" ratio) of the latex-avidin reagent was investigated. An A/C ratio of 0.25 was identified as providing an immunoassay that satisfied the parameters of a preferred phenytoin immunoassay. The assay was conducted using an assay buffer containing 0.01M phosphate buffer, 0.075M NaCl, 3.3% polyethylene glycol, 0.003% ethylenediaminetetraacetate (EDTA), 200 units/ml heparin, and 0.97% Triton X-100. The assay employed a buffer volume of 230 µl, a latex bidentate volume of 45 µl, an antibody volume of 30 µl, and a sample volume of 3 µl. Antibody was diluted 1/50. The results of the assay are shown in Table 5.

TABLE 5

| Phenytoin µg/ml | Rate | % B/B$_0$ |
| --- | --- | --- |
| 0 | 0.24086 | 100 |
| 2.5 | 0.19618 | 81.4 |
| 5 | 0.16045 | 66.6 |
| 10 | 0.12359 | 51.3 |
| 20 | 0.07554 | 31.4 |
| 40 | 0.04129 | 17.1 |

EXAMPLE 4

Use Of 60 Nm Latex Particles In A Latex Particle-Enhanced Homogeneous Immunoassay For Phenytoin: Optimization Of Assay Parameters The diameter of the particle used in the immunoassay controls the rate with which immunoprecipitation occurs. The standardization of a particle size decreases the cost and complexity of performing immunoassays for multiple analytes. Moreover, it permits the same reagents to be used in multiple immunoassays, and hence decreases the attendant costs of the assays. Since most analytes can be assayed using a 60 nm particle (parking area=100 Å$^2$/COOH), it is therefore desirable to employ particles having a diameter of 60 nm. For this reason immunoassays were evaluated for their capacity to satisfy the above-discussed desired parameters but using a 60 nm diameter particle.

The ascites fluids of six mice were screened for anti-phenytoin antibodies using 60 nm latex particle having an avidin-to-particle loading ratio ("A/C" ratio) of 0.15. The assay buffer was 0.01M phosphate buffer, 0.075M NaCl, 3.6% polyethylene glycol, 0.003% ethylenediaminetetraacetate (EDTA), 200 units/ml heparin, and 1.1% Triton X-100. The assay employed a buffer volume of 230 µl, a latex-bidentate volume of 45 µl, an antibody volume of 30 µl, and a sample volume of 3 µl. Antibody was diluted 1/50.

The ascites fluids of two animals (AS3 and AS8) showed good immunoreactivities and assay specificities as compared to other ascites fluids, however, they resulted in dose response curves that were much steeper than desired under the parameters (Table 6). Antibody from AS8 was selected for assay optimization as its dose response was closer to the desired parameters in terms of % B/B$_0$. Rate is expressed as (Δ(O.D.)/min)

TABLE 6

| Phenytoin | Antibody AS3 | | Antibody AS8 | |
| --- | --- | --- | --- | --- |
| µg/ml | Rate | % B/B$_0$ | Rate | % B/B$_0$ |
| 0 | 0.239 | 100 | 0.133 | 100 |
| 2.5 | 0.085 | 35.5 | 0.071 | 53.5 |
| 5 | 0.048 | 19.9 | 0.041 | 30.9 |
| 10 | 0.028 | 11.6 | 0.024 | 18.3 |
| 20 | 0.013 | 5.3 | 0.013 | 9.7 |
| 40 | 0.006 | 2.6 | 0.007 | 5.36 |

Several approaches can be used in order to obtain a more suitable dose response and rate. Based on the results shown in Table 6, dilution of the sample before assay will undoubtedly decrease the curve sensitivity and bring the dose response to within the desired parameters. Although this can be easily accomplished using automated equipment such as the ARRAY™ analyzer which has "on-board" sample dilution capability, it cannot be readily accomplished using analyzers such as the Synchron analyzer which lack such a sample dilution feature and the sample size used in already the minimal sample volume (3 µL neat) allowed by the instrument.

A second approach to improving the dose response curve of the immunoassay involves optimizing the avidin-to-particle loading ratio. To illustrate this approach, latex-avidin bidentate reagents were prepared using four different A/C ratios (0.25; 0.35; 0.45; 0.5). The particles were evaluated to determine if alterations in the A/C ratio provided an assay having desired parameters. Thus, identical immunoassays were conducted which varied only in the A/C ratio of the avidin-latex particle. The assay buffer used in these experiments was 0.01M phosphate buffer, 0.75M NaCl, 3.6% polyethylene glycol, 0.003% ethylenediaminetetraacetate (EDTA), 200 units/ml heparin, and 1.1% Triton X-100. The assay constituents and the calculated rates are shown in Table 7.

TABLE 7

| | A/C = 0.25 | | A/C = 0.35 | | A/C = 0.45 | | | | A/C = 0.50 | |
|---|---|---|---|---|---|---|---|---|---|---|
| CONSTITUENTS | | | | | | | | | | |
| Antibody Dilution | 1/50 | 1/30 | 1/30 | 1/30 | 1/50 | 1/50 | 1/75 | 1/75 | 1/50 | 1/75 |
| Latex Bidentate Dilution | Neat | Neat | 1:1.5 | 1:1.5 | Neat | Neat | Neat | Neat | Neat | Neat |
| Buffer (µl) | 230 | 230 | 230 | 220 | 230 | 230 | 230 | 230 | 230 | 230 |
| Latex Bidentate (µl) | 32 | 32 | 32 | 32 | 32 | 35 | 35 | 35 | 35 | 35 |
| Antibody (µl) | 30 | 30 | 30 | 40 | 40 | 40 | 40 | 40 | 40 | 40 |
| Sample (µl) | 3 | 3 | 3 | 3 | 3 | 3 | 3 | 3 | 3 | 3 |
| Phenytoin µg/ml) | RATE (ΔO.D./Min) | | | | | | | | | |
| 0 | 0.12365 | 0.09678 | 0.16412 | 0.18557 | 0.14329 | 0.16087 | 0.20633 | 0.24792 | 0.19733 | 0.21067 |
| 2.5 | 0.08302 | 0.07048 | 0.11254 | 0.11593 | 0.11485 | 0.13133 | 0.14456 | 0.14314 | 0.14606 | 0.15373 |
| 5 | — | — | — | 0.07768 | 0.0902 | 0.10469 | 0.11191 | 0.09355 | 0.12186 | 0.11358 |
| 10 | — | — | — | 0.0383 | 0.05764 | 0.06472 | 0.06311 | 0.05392 | 0.08144 | 0.06984 |
| 20 | — | — | — | 0.01707 | 0.02953 | 0.03372 | 0.03046 | 0.02093 | 0.0475 | 0.04014 |
| 40 | 0.00656 | 0.0084 | 0.014283 | 0.0076 | 0.01494 | 0.01505 | 0.01493 | 0.00809 | 0.02645 | 0.0224 |
| Phenyotin µg/ml | % B/B$_0$ | | | | | | | | | |
| 0 | 100 | 100 | 100 | 100 | 100 | 100 | 100 | 100 | 100 | 100 |
| 2.5 | 66.6 | 72.8 | 68.6 | 62.4 | 80.2 | 81.6 | 70.1 | 57.7 | 74 | 72.9 |
| 5 | — | — | — | 41.9 | 62.9 | 65.1 | 54.2 | 37.7 | 61.8 | 53.9 |
| 10 | — | — | — | 20.6 | 40.2 | 40.2 | 30.6 | 21.8 | 41.3 | 33.2 |
| 20 | — | — | — | 9.2 | 20.6 | 20.9 | 14.76 | 8.4 | 24.1 | 19.1 |
| 40 | 5.3 | 8.7 | 8.8 | 4.1 | 10.4 | 9.4 | 7.24 | 3.3 | 13.4 | 10.6 |

As seen in Table 7, at high A/C ratios (0.45–0.50) the % B/B$_0$ increased. However, none of the A/C ratios tested simultaneously brought both the reaction rate and dose response within the desired assay parameters. At an A/C ratio of ≧0.45, the reaction background from the latex material was high, and some significant non-specific reaction between the latex reagent and the buffer was observed.

EXAMPLE 5

Use Of 60 Nm Latex Particles In A Detergent-Facilitated, Latex Particle-Enhanced Homogeneous Immunoassay For Phenytoin In order to identify assay conditions that would permit the use of 60 nm particles in an immunoassay that satisfied the above-described desired assay parameters, the effect of polyethylene glycol and detergent on assay sensitivity and velocity was investigated.

Immunoassays were thus conducted using an assay buffer containing 0.01M phosphate buffer, 0.075M NaCl, either 3.6% or 4.4% polyethylene glycol ("PEG"), 200 units/ml heparin, and either 0% or 1.1% Triton X-100. Reactions containing Triton X-100 also contained 0.003% EDTA. The assays employed a buffer volume of 230 µl, a latex bidentate (1:1.5) volume of 32 µl, an antibody volume of 40 µl, and a sample volume of 3 µl. Antibody was diluted 1/50. The results of this analysis (shown in Table 8) reveal that PEG had a pronounced effect on assay rate, and that the inclusion of Triton X-100 substantially improved the dose response curve of the assay to optimum sensitivity. In the absence of Triton X-100, the reaction rate sharply decreased from 0 to 5 µg/ml and gradually leveled off at higher drag concentrations. This resulted in an undesired dose response which exhibited almost no discrimination between the effective drag concentration range (10–20 µg/ml) and the toxic level (>20 µg/ml). However, with the inclusion of Triton X-100, the curve became more "linearlized," and a good dose response was achieved across the entire assay range.

TABLE 8

| | CONSTITUENT | | |
|---|---|---|---|
| Triton-X | 0% | 0% | 1.1% |
| PEG | 4.4% | 3.6% | 3.6% |
| Phenytoin µg/ml | RATE (Δ(O.D.)/min) | | |
| 0 | 0.32228 | 0.14616 | 0.17177 |
| 2.5 | 0.23909 | 0.04658 | 0.11811 |
| 5 | 0.02539 | 0.02216 | 0.07422 |
| 10 | 0.01118 | 0.00851 | 0.04197 |
| 20 | 0.00292 | 0.00449 | 0.01968 |
| 40 | 0.00153 | 0.00221 | 0.01127 |
| Phenytoin µg/ml | % B/B$_0$ | | |
| 0 | 100 | 100 | 100 |
| 2.5 | 74.2 | 31.9 | 68.8 |
| 5 | 7.9 | 15.2 | 43.2 |
| 10 | 3.5 | 5.8 | 24.4 |
| 20 | 0.9 | 3.1 | 11.5 |
| 40 | 0.5 | 1.5 | 6.6 |

The effect of Triton X-100 concentration on the reaction rate and dose response was evaluated using the 60 nm latex particle (parking area of 110 Å$^2$/COOH) and an A/C avidin loading ratio of 0.45. The results of this evaluation are shown in Table 9.

TABLE 9

| | Triton X-100 1.1% | Triton X-100 1.6% | Triton X-100 2.1% |
|---|---|---|---|
| Phenytoin µg/ml | RATE (Δ(O.D.)/min) | | |
| 0 | 0.19421 | 0.19194 | 0.21324 |
| 2.5 | 0.13673 | 0.15234 | 0.17549 |
| 5 | 0.09731 | 0.12076 | 0.14421 |
| 10 | 0.05961 | 0.07755 | 0.09895 |

TABLE 9-continued

|  | Triton X-100 1.1% | Triton X-100 1.6% | Triton X-100 2.1% |
|---|---|---|---|
| 20 | 0.03296 | 0.0477 | 0.05926 |
| 40 | 0.01696 | 0.0229 | 0.0327 |
| Phenytoin µg/ml | | % B/B$_0$ | |
| 0 | 100 | 100 | 100 |
| 2.5 | 70.4 | 79.4 | 82.3 |
| 5 | 50.1 | 62.9 | 67.3 |
| 10 | 30.7 | 40.4 | 46.4 |
| 20 | 16.9 | 24.85 | 27.8 |
| 40 | 8.7 | 11.9 | 15.3 |

Table 9 shows that as the detergent concentration was increased, the reaction rate also increased with a concomitant decrease in the dose response (represented by % B/B$_0$). At 2.1% Triton X-100 in the assay buffer, the reaction rates were 0.21 Δ(O.D.)/min at 0 µg/ml and 0.0327 Δ(O.D.)/min at 40 µg/ml, and % B/B$_0$ ranged from 82.3% to 15.3% at 2.5 and 40 µg/ml, respectively. Thus, the incorporation of 2.1% Triton X-100 had successfully modulated the phenytoin assay sensitivity to within the desired assay parameters.

EXAMPLE 6

Variation Of Detergent Type In The Detergent-Facilitated, Latex Particle-Enhanced Homogeneous Immunoassay For Phenytoin In order to determine whether the desired assay parameters attained in Example 5 were dependent upon the use of Triton X-100 detergent, or whether other detergents could be equivalently employed, the above-described immunoassay was performed using Tween-20 instead of Triton X-100.

Immunoassays were thus conducted using an assay buffer containing 0.01M phosphate buffer, 0.75M NaCl, 3.3% polyethylene glycol ("PEG"), 0.003% EDTA, 200 units/ml heparin, and Tween-20 (at a concentration of either 1.1%, 2.1%, 2.6%, or 3.1%. The assays employed a buffer volume of 230 µl, a latex bidentate (1:1.5) volume of 32 µl, an antibody volume of 40 µl, and a sample volume of 3 µl. Antibody was diluted 1/50. The A/C ratio was 0.35. The results of this analysis are shown in Table 10.

TABLE 10

| CONSTITUENT | | | | | |
|---|---|---|---|---|---|
| Tween-20 | 1.1% | 2.1% | 2.6% | 3.1% | 0% |
| Triton X-100 | 0% | 0% | 0% | 0% | 3.1% |
| Phenytoin µg/ml | | | RATE (ΔO.D./MIN.) | | |
| 0 | 0.15736 | 0.12513 | 0.14040 | 0.16533 | 0.25895 |
| 2.5 | 0.08886 | 0.07826 | 0.09966 | 0.13013 | 0.20378 |
| 5 | 0.05356 | 0.05358 | 0.07447 | 0.09718 | 0.16099 |
| 10 | 0.02236 | 0.03388 | 0.04627 | 0.06497 | 0.10419 |
| 20 | 0.01306 | 0.01359 | 0.02186 | 0.03092 | 0.05477 |
| 40 | 0.00567 | 0.00663 | 0.01176 | 0.01556 | 0.02754 |
| Phenytoin µg/ml | | | % B/B$_0$ | | |
| 0 | 100 | 100 | 100 | 100 | 100 |
| 2.5 | 56.5 | 62.5 | 70.9 | 78.7 | 78.7 |
| 5 | 34 | 42.8 | 53 | 58.8 | 62.2 |
| 10 | 14.2 | 27.1 | 32.9 | 39.3 | 40.2 |
| 20 | 8.3 | 10.9 | 15.6 | 18.7 | 21.2 |
| 40 | 3.6 | 5.3 | 8.4 | 9.4 | 10.6 |

As indicated in Table 10, the use of Tween-20 resulted in an improvement to the dose response of the immunoassay that was similar to that observed with Triton X-100. Triton X-100 is a preferred detergent since its use resulted in a substantially higher reaction rate than that obtained using Tween 20. Moreover, a lower Triton X-100 concentration was required in order to achieve the desired dose response and reaction rate assay parameters. The results indicate that the improvement in the dose response of an immunoassay is not limited to a specific class of detergents.

EXAMPLE 7

Detergent-Facilitated, Latex Particle-Enhanced Homogeneous Immunoassay For Phenobarbital The above-described, detergent-facilitated, latex particle-enhanced homogeneous immunoassay format may be used to assay the concentration or presence of any analyte. To demonstrate the general nature of the invention, the methods of the present invention were used to assay for phenobarbital. Phenobarbital (5-ethyl-5-phenyl-2,4,6 (1H,3H,-pyrimidinetrione)) is an anti-convulsant. It is additionally used as a sedative and as a hypnotic; Phenobarbital is also a substance of abuse (Chao, M. K. C. et al., In: *Analytical Profiles of Drug Substances*, volume 5, Florey, K. (ed.), Academic Press, New York, pp. 359–399 (1978).

Immunoassays were conducted using an assay buffer containing 0.01M phosphate buffer, 0.75M NaCl 3.6% polyethylene glycol ("PEG"), 0.003% EDTA, 200 units/ml heparin, and Triton X-100 (at a concentration of either 1.1%, 1.6% or 2.1%. The assays employed a buffer volume of 230 µl, 32 µl of a 60 nm diameter latex particle-avidin-biotin-phenobarbital bidentate (1:1.16), an antibody volume of 45 µl, and a sample volume of 3 µl. The A/C ratio of the latex particle was 0.45. The read window was 16–48 seconds after the antibody trigger was introduced. The results of this analysis are shown in Table 11.

TABLE 11

| Phenobarbital | Triton X-100 Concentration | | |
|---|---|---|---|
| µg/ml | 1.1% | 1.6% | 2.1% |
| | RATE (ΔO.D./MIN.) | | |
| 0 | 0.27988 | 0.27986 | 0.27393 |
| 5 | 0.21493 | 0.23031 | 0.25663 |
| 10 | 0.16181 | 0.18605 | 0.21547 |
| 20 | 0.10759 | 0.13007 | 0.15228 |
| 40 | 0.05337 | 0.07464 | 0.08809 |
| 80 | 0.02643 | 0.03524 | 0.04477 |
| | % B/B$_0$ | | |
| 0 | 100 | 100 | 100 |
| 5 | 76.8 | 82.3 | 93.7 |
| 10 | 57.8 | 66.5 | 78.7 |
| 20 | 38.4 | 46.5 | 55.6 |
| 40 | 19.1 | 26.7 | 32.2 |
| 80 | 9.4 | 12.6 | 16.3 |

As indicated in Table 11, the use of Triton X-100 in the immunoassay permitted the use of 60 nm particles in an immunoassay that conformed to the above-discussed desired parameters, thereby demonstrating the general applicability of the invention While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

What is claimed is:

1. An immunoassay for determining the presence of a target analyte in a test sample comprising the steps of:
    (1) forming a reaction mixture by contacting a test sample with an anti-target analyte antibody capable of binding to a target analyte, a soluble bidentate reagent, a biotin-binding agent selected from the group consisting of avidin and streptavidin, and a detergent, wherein the detergent is present in the reaction mixture at a selected concentration greater than about 1%, and wherein the soluble bidentate reagent comprises a biotin member, an analyte member, and a spacer member, wherein:
        (i) the biotin member of the reagent is capable of binding to the biotin-binding agent, the biotin-binding agent being immobilized to a solid support;
        (ii) the analyte member of the bidentate reagent is capable of specifically binding to the anti-target analyte antibody; and
        (iii) the intermediate spacer member is of sufficient length to permit the analyte member to bind to the anti-target analyte antibody and the biotin member to bind to the biotin-binding agent simultaneously;
    (2) incubating the reaction mixture under conditions sufficient to permit the formation of a complex among the bidentate reagent, the biotin-binding agent, and the anti-target analyte antibody; and
    (3) determining the presence of the target analyte in the test sample by measuring the extent of any formation of the complex, the extent being inversely proportional to the concentration of the target analyte in the sample, and wherein the selected concentration of detergent is determined by the steps of:
        (a) identifying a first, non-zero physiologically relevant, calibrator concentration of the target analyte;
        (b) identifying a second, physiologically relevant, calibrator concentration of the target analyte, wherein the second calibrator concentration is higher than the first calibrator concentration;
        (c) performing steps (1), (2), and (3) at different test detergent concentrations until there is achieved an immunoassay having:
            i) a rate of complex formation greater than about 0.2 O.D. units per minute at a concentration of the target analyte of 0 µg/ml;
            ii) a rate of complex formation greater than about 0.02 O.D. units per minute at the second calibrator concentration;
            iii) a rate of complex formation at the first calibrator concentration equal to at least about 75% of the reaction rate at a concentration of the target analyte of 0 µg/ml; and
            iv) a rate of complex formation at the second calibrator concentration of less than 25% of the reaction rate at a concentration of the target analyte of 0 µg/ml.

2. The immunoassay of claim 1 wherein the detergent is selected from the group consisting of alkylpolyoxyethylene ether, alkylphenylpolyoxyethylene ether and acylpolyoxyethylene sorbitan ester.

3. The immunoassay of claim 2 wherein the detergent is alkylphenylpolyoxyethylene ether.

4. The immunoassay of claim 1 wherein the target analyte is selected from the group consisting of phenytoin and phenobarbital.

5. The immunoassay of claim 1 wherein:
    (i) the target analyte is phenytoin;
    (ii) the first calibrator concentration is about 2.5 micrograms per milliliter; and
    (iii) the second calibrator concentration is about 40 micrograms per milliliter.

6. The immunoassay method of claim 1 wherein the detergent is selected from the group consisting of alkylpolyoxyethylene ether, alkylphenylpolyoxyethylene ether and acylpolyoxyethylene sorbitan ester.

7. The immunoassay of claim 1 wherein:
    i) the target analyte is phenobarbital;
    ii) the first calibrator concentration is about 5 micrograms per milliliter; and
    iii) the second calibrator concentration is about 80 micrograms per milliliter.

8. The immunoassay of claim 1, wherein the solid support is a particle and has a diameter from about 38 nanometers to about 100 nanometers.

9. The immunoassay of claim 8 wherein the particle has a diameter of about 60 nanometers.

10. The immunoassay of claim 1 wherein the solid support is latex.

11. An immunoassay for determining the presence of a target analyte in a test sample comprising the steps of:
    (1) forming a reaction mixture by contacting a test sample with an anti-target analyte antibody capable of binding to a target analyte, a bidentate reagent, and a detergent, wherein the detergent is present in the reaction mixture at a selected concentration greater than about 1%, and wherein the soluble bidentate reagent comprises a biotin member, an analyte member, and a spacer member between the biotin and analyte members, wherein:
        (i) the biotin member of the reagent is capable of binding to a biotin-binding agent selected from the group consisting of avidin and streptavidin, the biotin-binding agent being immobilized to a solid support;
        (ii) the analyte member of the bidentate reagent is capable of specifically binding to the anti-target analyte antibody;
        (iii) the intermediate spacer member is of sufficient length to permit the analyte member to bind to the anti-target analyte antibody and the biotin member to bind to the biotin-binding agent simultaneously; and
        (iv) wherein the bidentate reagent is attached to the biotin-binding agent;
    (2) incubating the reaction mixture under conditions sufficient to permit the formation of a complex between the bidentate reagent and the anti-target analyte antibody; and
    (3) determining the presence of the target analyte in the test sample by measuring the extent of any formation of the complex, the extent being inversely proportional to the concentration of the target analyte in the sample, and wherein the selected concentration of detergent is determined by the steps of:

(a) identifying a first, non-zero physiologically relevant, calibrator concentration of the target analyte;

(b) identifying a second, physiologically relevant, calibrator concentration of the target analyte, wherein the second calibrator concentration is higher than the first calibrator concentration;

(c) performing steps (1), (2), and (3) at different test detergent concentrations until there is achieved an immunoassay having:

i) a rate of complex formation greater than about 0.2 O.D. units per minute at a concentration of the target analyte of 0 µg/ml;

ii) a rate of complex formation greater than about 0.02 O.D. units per minute at the second calibrator concentration;

iii) a rate of complex formation at the first calibrator concentration equal to at least about 75% of the reaction rate at a concentration of the target analyte of 0 µg/ml; and iv) a rate of complex formation at the second calibrator concentration of less than 25% of the reaction rate at a concentration of the target analyte of 0 µg/ml.

12. The immunoassay of claim 11 wherein the detergent is selected from the group consisting of alkylpolyoxyethylene ether, alkylphenylpolyoxyethylene ether and acylpolyoxyethylene sorbitan ester.

13. The immunoassay of claim 12 wherein the detergent is alkylphenylpolyoxyethylene ether.

14. The immunoassay of claim 11, wherein the solid support is a particle and has a diameter from about 38 nanometers to about 100 nanometers.

15. The immunoassay of claim 14 wherein the particle has a diameter of about 60 nanometers.

16. The immunoassay of claim 11 wherein the solid support is latex.

17. The immunoassay of claim 11 wherein:

the target analyte is phenytoin;

ii) the first calibrator concentration is about 2.5 micrograms per milliliter; and iii) the second calibrator concentration is about 40 micrograms per milliliter.

18. The immunoassay of claim 17 wherein the detergent is selected from the group consisting of alkylpolyoxyethylene ether, alkylphenylpolyoxyethylene ether and acylpolyoxyethylene sorbitan ester.

19. The immunoassay of claim 11 wherein the target analyte is selected from the group consisting of phenytoin and phenobarbital.

20. The immunoassay of claim 11 wherein:

i) the target analyte is phenobarbital;

ii) the first calibrator concentration is about 5 micrograms per milliliter; and iii) the second calibrator concentration is about 80 micrograms per milliliter.

21. A homogeneous immunoassay for determining the presence of a target analyte in a test sample comprising the steps of:

(1) forming a reaction mixture by contacting a test sample with an anti-target analyte antibody capable of binding to a target analyte, a bidentate reagent, a bidentate-binding agent capable of binding to the bidentate reagent, the bidentate-binding agent being immobilized on a latex particle, and a detergent, wherein the detergent is present in the reaction mixture at a selected concentration greater than about 1%, and wherein the bidentate reagent comprises a biotin member, an analyte member, and a spacer member, wherein:

(i) the biotin member of the reagent is capable of binding to the biotin-binding agent, (ii) the analyte member of the bidentate reagent is capable of specifically binding to the anti-target analyte antibody; and (iii) the intermediate spacer member is of sufficient length to permit the analyte member to bind to the anti-target analyte antibody and the biotin member to bind to the biotin-binding agent simultaneously;

(2) incubating the reaction mixture under conditions sufficient to permit the formation of a complex of the bidentate reagent, the bidentate-binding agent immobilized on a latex particle, and the anti-target analyte antibody; and (3) determining the presence of the target analyte in the test sample by measuring the extent of any formation of the complex, the extent being inversely proportional to the concentration of the target analyte in the sample, wherein the selected concentration of detergent to use in the homogeneous immunoassay is determined by the steps of:

(a) identifying a first, non-zero physiologically relevant, calibrator concentration of the target analyte;

(b) identifying a second, physiologically relevant, calibrator concentration of the target analyte, wherein the second calibrator concentration is higher than the first calibrator concentration;

(c) performing steps (1), (2), and (3) at at least two different test detergent concentrations until there is achieved an immunoassay having:

i) a rate of complex formation greater than about 0.2 O.D. units per minute at a concentration of the target analyte of 0 µg/ml;

ii) a rate of complex formation greater than about 0.02 O.D. units per minute at the second calibrator concentration;

iii) a rate of complex formation at the first calibrator concentration equal to at least about 75% of the reaction rate at a concentration of the target analyte of 0 µg/ml; and iv) a rate complex formation at the second calibrator concentration of less than 25% of the reaction rate at a concentration of the target analyte of 0 µg/ml, wherein the detergent is selected from the group consisting of alkylpolyoxyethylene ether, alkylphenylpolyoxyethylene ether and acylpolyoxyethylene sorbitan ester, and wherein the latex particle has a diameter from about 38 nanometers to about 100 nanometers.

22. The immunoassay of claim 21 wherein the latex particle is heat stressed.

23. The immunoassay of claim 21 wherein the bidentate-binding agent is selected from the group consisting of avidin and streptavidin.

24. The immunoassay of claim 21 wherein the latex particle has a diameter of about 60 nanometers.

25. The immunoassay of claim 21 wherein the target analyte is selected from the group consisting of phenytoin and phenobarbital.

26. The immunoassay of claim 21 wherein:
the target analyte is phenytoin;
ii) the first calibrator concentration is about 2.5 micrograms per milliliter; and
iii) the second calibrator concentration is about 40 micrograms per milliliter.

27. The immunoassay of claim 21 wherein:
i) the target analyte is phenobarbital;
ii) the first calibrator concentration is about 5 micrograms per milliliter; and
iii) the second calibrator concentration is about 80 micrograms per milliliter.

28. The immunoassay of claim 21 wherein the detergent is alkylphenylpolyoxyethylene ether.

* * * * *